United States Patent [19]

Vadas et al.

[11] 4,340,367
[45] Jul. 20, 1982

[54] LOADER AND DISPENSER FOR DENTAL AMALGAM

[76] Inventors: Leslie Vadas, 135 Riviera Dr., Los Gatos, Calif. 95030; Bert M. Sabo, 19200 Bountiful Acres, Saratoga, Calif. 95070

[21] Appl. No.: 216,147

[22] Filed: Dec. 15, 1980

[51] Int. Cl.$^3$ .............................................. A61C 5/04
[52] U.S. Cl. .................... 433/89; 141/249; 222/391
[58] Field of Search ............ 433/89, 83, 90, 80; 141/249, 2, 18, 386; 222/252, 253, 256, 391, 340

[56] References Cited

U.S. PATENT DOCUMENTS

| | | | |
|---|---|---|---|
| 2,086,462 | 7/1937 | Bost | 32/70 |
| 2,438,843 | 3/1948 | Correa | 222/391 |
| 2,541,949 | 2/1951 | Thacker et al. | 222/391 |
| 2,768,768 | 10/1956 | Cornell et al. | 222/391 |
| 3,221,409 | 12/1965 | Thiel et al. | 32/60 |
| 3,293,749 | 12/1966 | George et al. | 32/60 |
| 3,322,307 | 5/1967 | Fraser | 222/207 |
| 3,537,617 | 11/1970 | Mendola | 222/340 |
| 3,985,166 | 10/1976 | Klee | 141/386 |
| 4,173,236 | 11/1979 | Hirdes | 433/89 |

FOREIGN PATENT DOCUMENTS

| | | | |
|---|---|---|---|
| 642306 | 3/1937 | Fed. Rep. of Germany | 433/83 |
| 2442626 | 6/1980 | France | 433/229 |
| 934235 | 8/1963 | United Kingdom | 433/89 |

*Primary Examiner*—Hugh R. Chamblee
*Assistant Examiner*—John J. Wilson
*Attorney, Agent, or Firm*—C. E. Tripp

[57] ABSTRACT

A dental amalgam dispenser unit having a detachable discharge head, the dispenser having a plunger with a front amalgam-advancing tip and rearwardly disposed ratchet teeth and a pawl comprising a slidably mounted sleeve and a cantilever spring projecting rearwardly therefrom. A dental amalgam loader assembly is also described for loading the dispenser discharge head. The loader has a plunger and advancing means for advancing the forward portion of the loading plunger a predetermined distance into the bore of the dispenser head.

9 Claims, 13 Drawing Figures

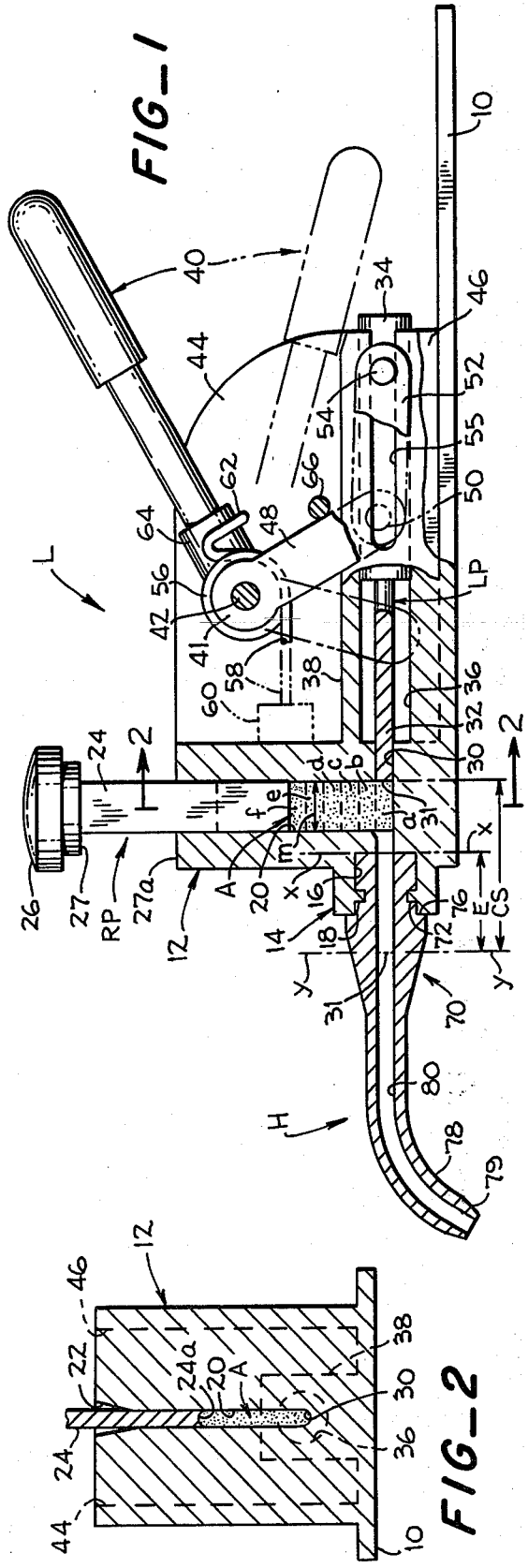
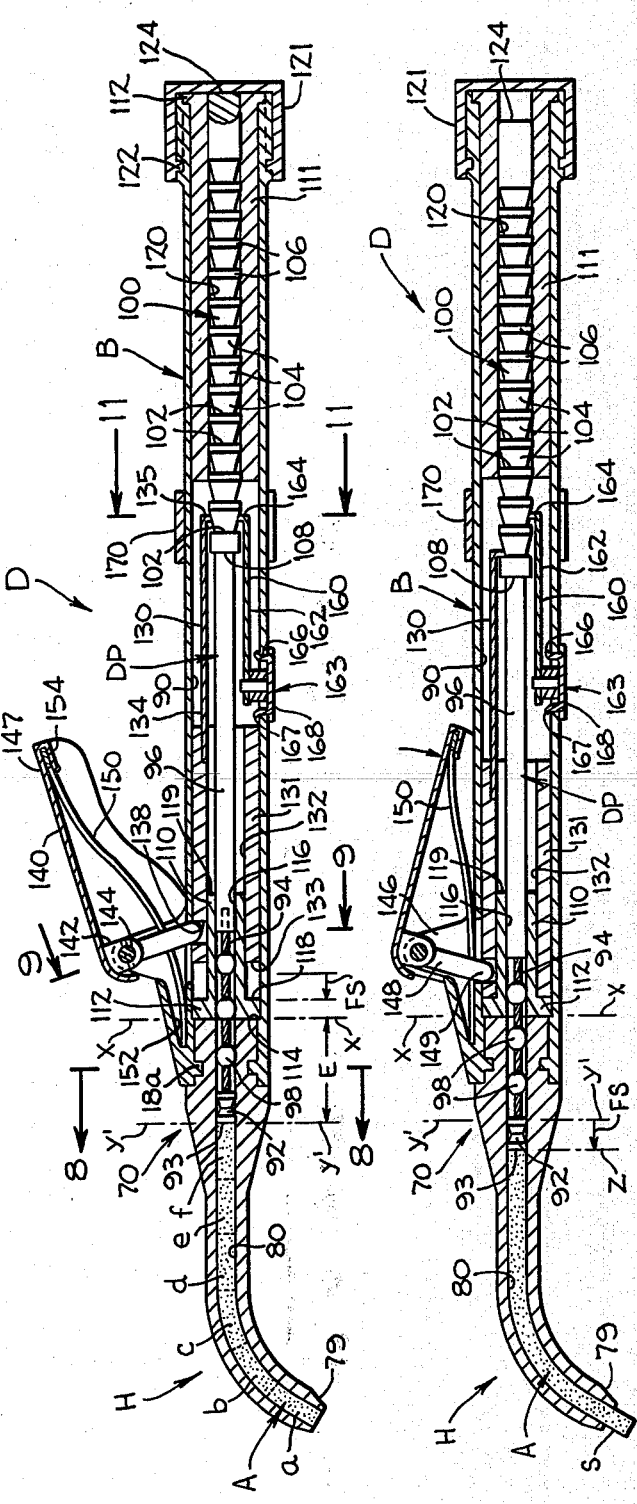
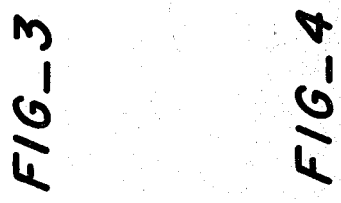

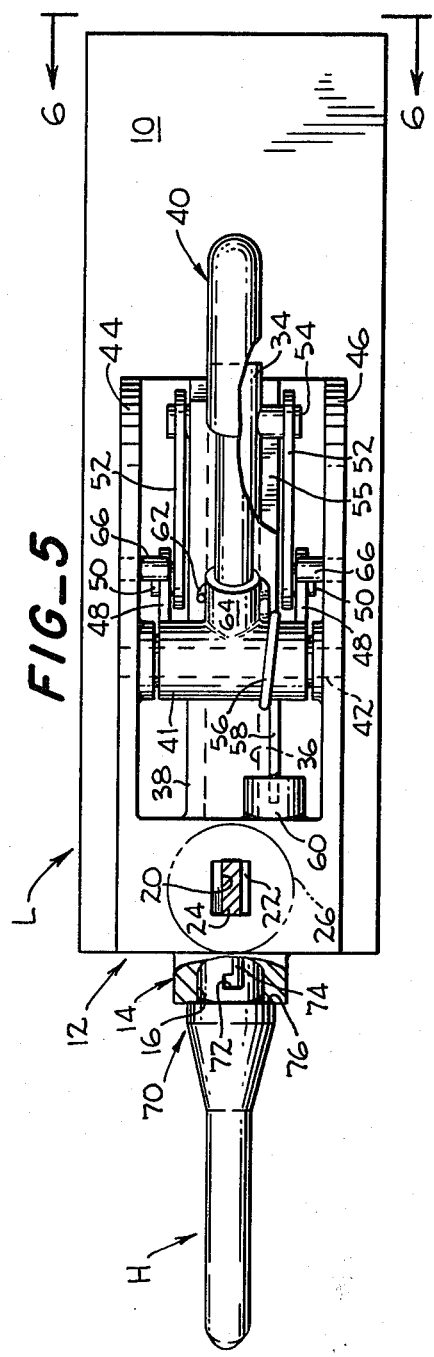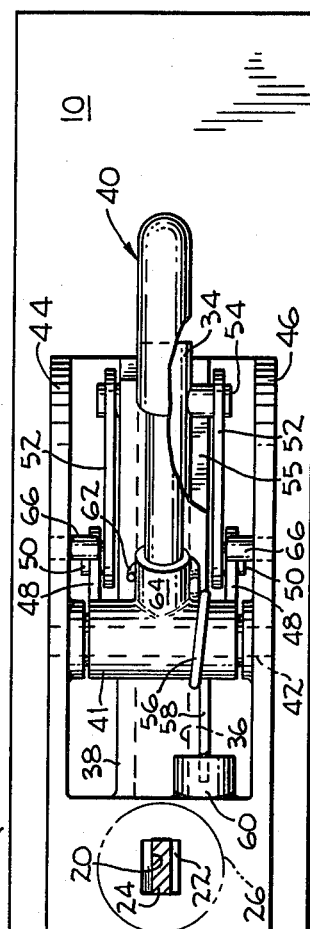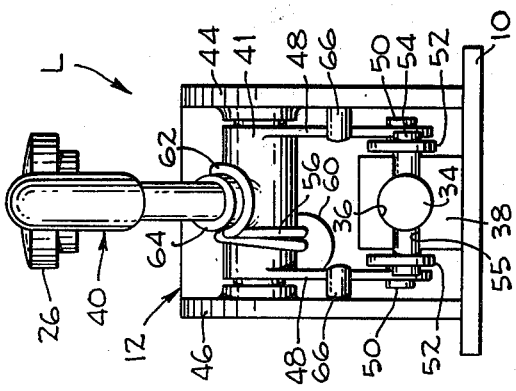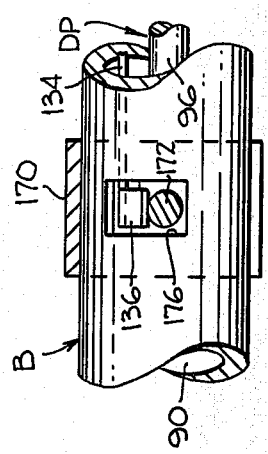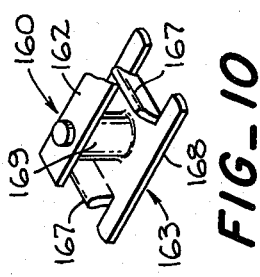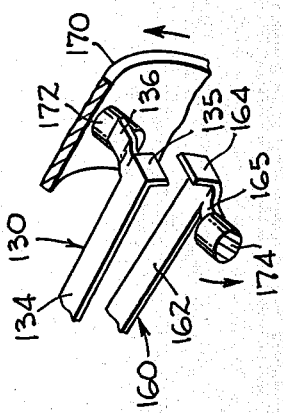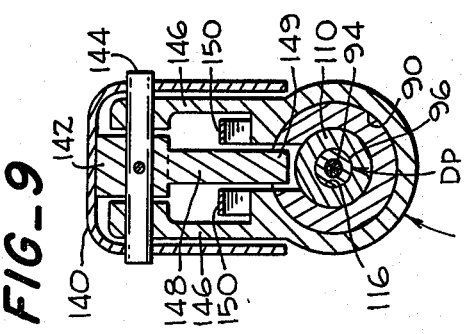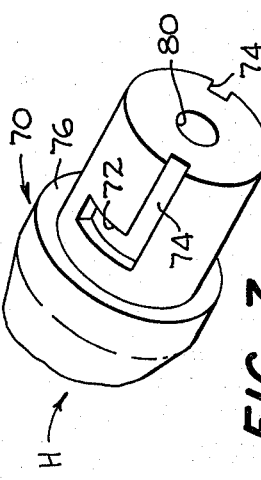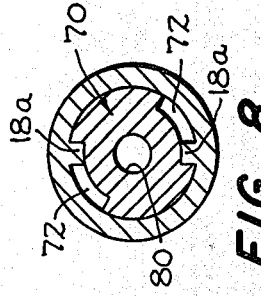

LOADER AND DISPENSER FOR DENTAL AMALGAM

FIELD OF THE INVENTION

This invention relates to the dispensing of dental amalgam into a tooth cavity and more particularly a sequentially operated amalgam dispenser unit and a system for loading amalgam into a dispensing head, associated with the dispenser unit.

SUMMARY OF THE INVENTION

Broadly speaking, an amalgam dispenser has an attachable discharge head or dispensing tip, to be referred to as the "head", a body or handle for mounting the head and having a plunger for advancing amalgam along a bore in the head. Such devices are generally known in the art.

One of the features of the subject invention resides in a system for loading the head of such a dispenser with amalgam before it is attached to a body or handle unit, the unit having an amalgam advancing plunger. In accordance with the present invention, the breech portion of the head is first mounted on a loading unit that contains a supply of premixed amalgam. Amalgam is pushed from the loading unit into a bore in the head until the head is filled with amalgam from the outer end of its bore back to a predetermined position in the breech portion of the head. This breech portion of the head is occupied by the outer end of a plunger in the handle when a loaded head is mounted on the handle and when the plunger in the handle is fully retracted. This system insures clean transfer (no amalgam drop-out) of the loaded head from the loading unit to the handle with a predetermined charge of amalgam being confined within the bore of the head. Furthermore, when the loaded head is mounted on the handle, amalgam is discharged from the head as soon as advance of the plunger in the handle is initiated.

Another feature of the invention relates to a discharge or dispensing head loader that has a body formed with an amalgam reservoir passage and a connector that detachably receives the head. The loader has a loading plunger that successively shears off slugs of amalgam at the intersection of the reservoir passage and an amalgam loading bore or passage formed in the loader body. The plunger continues to advance and pushes the slugs end-to-end into a bore in the attached discharge head.

The invention includes an amalgam dispensing unit made up of a dispensing or discharge head that is quickly attachable to an amalgam metering body, to be referred to as the "handle". The handle is hollow and slidably mounts a dispensing plunger having a front amalgam-advancing tip and rearward ratchet teeth. The handle has an internally mounted plunger-advancing pawl which is preferably mounted on a sleeve and the sleeve is slidably mounted in the hollow of the handle. An actuator lever mounted on the handle advances the sleeve, pawl and plunger for discharging amalgam from a previously loaded head, mounted on the handle.

The rear end of the handle is closed by a removable cap. In order to clean and sterilize the handle and associated parts, the cap is removed and the plunger can be pushed rearwardly out of the handle. This plunger removal action is facilitated by the provision of a ratchet release device mounted on the handle.

In the preferred embodiment of the invention, a fixed pawl is mounted in the handle for restraining retraction of the dispensing plunger. The pawl-release device also releases the fixed pawl from the plunger ratchet teeth so that the plunger can be readily retracted or removed, as described.

The preferred pawl-release device includes a collar that is rotatably mounted on the handle and having a lug that projects through a slot in the handle. The lug engages and retracts the plunger-advancing pawl from the plunger ratchet. When both moveable and fixed pawls are provided, a second lug on the release device retracts the fixed pawl for accommodating plunger retraction or withdrawal.

The preferred pawl construction comprises a cantilever spring mounted at its forward end and projecting rearwardly, with a pawl tooth projecting radially from a rearward portion of the spring. The pawls are mounted within the hollow handle and the moveable pawl is advanced by a manual lever pivotally supported on the handle and having pawl-advancing arm projecting through a slot in the handle.

The manner in which the aforesaid features and advantages are provided will be apparent to those skilled in the art from the following detailed description of a preferred embodiment of the invention.

IN THE DRAWINGS

FIG. 1 is a side view of the loader and a mounted dispensing head with parts broken away.

FIG. 2 is a partial section through the loader taken on line 2—2 of FIG. 1.

FIG. 3 is a section through the dispenser unit and a fully loaded head with the dispensing plunger fully retracted.

FIG. 4 is a section like that of FIG. 3 with the plunger advanced on the first stroke.

FIG. 5 is a plan view of the loader with the actuator.

FIG. 6 is an end view of the loader looking along line 6—6 of FIG. 5.

FIG. 7 is an enlarged partial perspective of the dispensing tip breech.

FIG. 8 is an enlarged section through the breech assembly taken on line 8—8 of FIG. 3.

FIG. 9 is an enlarged section through the dispenser taken on line 9—9 of FIG. 3.

FIG. 10 is a perspective view of the clip mounting for the fixed pawl.

FIG. 11 is an enlarged section through the dispenser handle taken along line 11—11 of FIG. 3.

FIG. 12 is an enlarged section through the pawl release collar taken along line 12—12 of FIG. 11.

FIG. 13 is a partial perspective of the pawl release mechanism.

DETAILED DESCRIPTION OF A PREFERRED EMBODIMENT

General Description

FIG. 1 is a side view of a loader unit L detachably mounting a dispensing or discharge head H. Initially, the loader is charged with a measured amount of amalgam A for mixing, preferably from a mixing and charging unit (not shown) known in the art. The loader L is then operated to load the head H with amalgam for subsequent utilization of the head on an amalgam dispenser unit.

FIG. 3 shows a dispensing unit D having an amalgam-loaded head H fitted to a body or handle B. The dentist operates an actuator lever on a handle to successively discharge slugs of amalgam such as a first slug "s", seen in FIG. 4. A more detailed description of the operation will follow a detailed description of the parts.

Loader

Referring to FIGS. 1, 2, 5 and 6, the loader L has a base plate 10 that supports an upstanding body portion 12. A bayonet joint socket or breech 14 projects forwardly from the lower front of the body 12 and has a bore 16 formed with two circumferentially spaced bayonet joint lugs 18 for mounting a breech portion of the head H.

The body 12 is formed with an amalgam reservoir passage 20 which is charged with amalgam A. As seen in FIG. 5, the reservoir passage 20 is rectangular in section with the long axis of the section vertically disposed. The passage has an upper, diverging wall mouth 22 (FIGS. 1 and 5) to facilitate loading of the reservoir passage 20. As best seen in FIG. 1, a replenishing plunger RP has a stem 24 which is rectangular in section and slidingly fits the rectangular section reservoir passage 20. A knob 26 on the upper end of stem 24 facilitates insertion of the replenishing plunger RP into the loader, followed by manual advance of the plunger during the loading operation.

As seen in FIG. 1, and in order to provide a passage for the loading of amalgam into the dispensing head, the loader body portion 12 is formed with a longitudinal feed or loading bore 30. The bore extends through the upstanding body portion 12 into the bore 16 of the breech 14 and intersects the lower end of the reservoir passage 20. A loading plunger LP has a forward portion 32 that slidingly fits the body bore 30 and an enlarged rear portion 34. The rear portion 34 slides in a bore 36 formed in an elongate longitudinal rib 38 (FIGS. 1, 5 and 6).

As best seen in FIGS. 1 and 5, the tip loading plunger LP is manually advanced and retracted by a loading lever 40 having a hub 41 that is pivotally mounted on a pin 42 extending between upright ears 44 and 46. Spaced actuating arms 48 project down from the hub 41. The lower end of each arm is pivoted to a link pin 50 projecting from the forward end of a short link 52. The links 52 straddle the hub 38 and extend rearwardly to pivotally mount a cross pin 54. The rib 38 is transversely slotted at 55 to slidingly receive the cross pin 54 and the pin extends through the rear portion 34 of the loading pin LP. Thus, lowering of lever 40 advances the loading pin and raising the lever retracts it.

The lever 40 is urged to its raised position by a spring 56 having a forward leg 58 retained by a body boss 60 and a rearward leg 62 that is hooked around a lever hub extension 64. Stop pins 66 limit retraction of arms 48.

Head Mounting

FIGS. 1 and 5 show a discharge head or dispensing tip H (to be referred to as the "head") detachably mounted in the breech 14 of the loader unit for receiving amalgam from the loader.

The head H has a breech portion 70 that is received in the breech bore 16 of the loader and is formed with circumferential slots 72 that receive the lugs 18 on the loader breech portion. As seen in FIG. 7, the breech 70 is also formed with longitudinal slots 74 for accommodating entry of the loader lugs 18 into the circumferential slots 72 formed in the breech portion of the head. This construction provides a quick attachable and detachable bayonet joint mounting for the head. A radial flange 76 at the breech portion of the head H cooperates with the loader breech portion 14 and the bayonet joint elements just described to provide a snug friction fit of the head with the loader.

Referring principally to FIG. 1, the outer end of the head is curved downwardly at 78 to facilitate direction of amalgam into a tooth cavity. The discharge or tip end of the head is bevelled or conical as shown at 79. An amalgam receiving and discharge bore 80 extends through the entire length of the head H. The rearward portion of the bore 80 is straight and concentric with the loading bore 30 formed in the loader. Thus, when the loading plunger LP is advanced, the front portion 32 of the plunger extends into the straight portion of bore 80 in the head H at the breech portion of the head.

Loader Operation

In operation, the replenishing plunger RP is removed from the loader and the reservoir passage 20 of the loader is charged with a body of pre-mixed amalgam A. Preferably, the amount of amalgam placed in the reservoir passage 20 equals the amount of amalgam needed to substantially but not completely fill the bore 80 in the head H. The amount of amalgam is such that it will fill the bore 80 back from its discharge end to the position occupied by the front face 31 of the tip loading plunger 32 when the latter is fully advanced. The advanced position of plunger face 31 is shown in dotted lines in FIG. 1. The advanced position is reached when the loading plunger LP is advanced from its retracted position through the length of a charging stroke CS, indicated by an arrow on FIG. 1.

In order to load or charge the bore 80 in the head H, the loading plunger LP is repeatedly advanced and retracted by operation of the loader lever 40. As the forward portion 32 of the loading plunger LP advances through the intersection of the reservoir passage 20 and the loading bore 30, the front end face 31 of the plunger shears off a slug of amalgam at the intersection and advances it through the straight portion of bore 80 in the breech 70 of the head H. During this operation, a light manual pressure can be applied to the knob 26 on the replenishing plunger RP to insure that the amalgam is properly compacted during the loading operation.

The loading plunger LP is now retracted to its retracted position shown in FIG. 1 and the front face 31 of the plunger is returned to a position flush with the rear wall of the reservoir passage 20. Pressure is applied to the replenishing plunger knob 26 so that the intersection of the reservoir passage 20 and the loading bore 30 is again filled with amalgam. The loading lever 40 is now depressed to advance the loading plunger portion 32 across the passage intersection a second time, thereby shearing off a second slug of amalgam and advancing it into the bore 80 of the head H. This slug engages the previously deposited slug in the bore and pushes it end-to-end further along the bore 80.

The aforesaid operations are repeated until the body of amalgam A charged into the reservoir passage 20 and into the inner section of that passage and the bore 30 has been transferred into the bore 80 of the head H. At this time, the stem 24 of the replenishing plunger RP will be in its fully lowered position (not shown) and a stop face 27 formed on the knob 26 will be in engagement with the stop face 27a on the upper portion of the body 12 of the loader. As seen in FIG. 2, the lower end face 24a of the stem 24 is formed as a section of a semi-circle of the same diameter as the diameter of the loading bore 30 formed in the loader body. Thus, when the stem 24 is fully lowered, the lower end face 24a of the stem 24 forms a continuation of the upper wall of the loading bore 30 across the intersection between the reservoir passage 20 and that bore. This construction insures that the loader will be completely cleared of amalgam by operation of the loading plunger LP and thus facilitates cleaning of the loader after use.

In the embodiment shown, the amount of amalgam being discharged into the loader reservoir passage 20 and the intersection thereof with the bore 30 is such that the volume represents that of six slugs a-f of amalgam to be sheared off by sequential advance of the loading plunger LP. The six "incipient" slugs a-f representing the volume of amalgam A in the loader are indicated by dotted lines in FIG. 1 and those same slugs a-f are shown charged into the dispensing head H by dotted lines in FIG. 3.

Dispensing Instrument

A complete amalgam dispensing instrument D is shown in FIGS. 3 and 4 and FIGS. 7-13 illustrate various details thereof.

FIG. 3 shows a fully charged head H assembled with the handle B which serves as an amalgam dispensing or metering unit. The hollow handle B has a through-bore 90, the forward portion of which provides a bayonet joint socket for the breech portion 70 of the head H. This construction includes radial bayonet joint lugs 18a that function to retain the head, as do the lugs 18 on the loader L, previously described.

Dispensing Plunger

Slidably mounted in the hollow handle B is a dispensing plunger DP having a front amalgam-advancing tip 92 formed with a front end face 93. When the head H is mounted on the dispenser unit D, the plunger tip 92 projects into the unfilled portion of the bore 80 in the dispenser head when the tip is retracted.

The plunger tip 92 is mounted on the front end of a closely wound wire cable 94, the rear end of the cable projecting from a cylindrical plunger rod 96. Guide beads 98 are mounted along the cable 94.

The rearward portion of the dispensing plunger DP is formed as a circular section ratchet 100. The ratchet provides a series of rearwardly facing ratchet teeth 102 with intervening conical pawl camming surfaces 104. Cylindrical guide lands 106 are provided. A stop face 108 for limiting advance of the plunger is formed at the front end of ratchet 100.

The dispensing plunger DP is slidably mounted in the hollow handle B by means of front and rear sleeves 110, 111. The front sleeve 110 has a head flange 112 that is pressed into the handle bore 90 against a small stop shoulder 114 at the head-receiving breech portion of the bore 90. The sleeve 110 has a central bore 116 for slidably receiving the cable beads and the plunger rod 96 of the dispensing plunger. The sleeve flange 112 has a rearwardly facing stop face 118 for limiting advance of a pawl actuator sleeve, to be described. The rear end of sleeve 110 provides a stop face 119 for the plunger stop face 108.

The ratchet 100 of the dispensing plunger DP is slidably mounted in a central bore 120 formed in the rear sleeve 111. The rear end of sleeve 111 is flanged at 112 so that the sleeve is removably secured in the bore 90 of the handle B by a removable cap 121. The cap 121 is mounted on the handle by a bayonet joint construction 122, such as those previously described. Retraction of the dispensing plunger DP is limited by engagement of a rear end face 124 of the plunger with the cap 121, as shown in FIG. 3.

Plunger Advancing Pawl Assembly

As best seen in FIGS. 3 and 4, the plunger advancing pawl assembly 130 is mounted in the hollow handle B. The assembly includes a pawl actuator sleeve 131 that slides in the handle bore 90 and has a central bore 132, the front portion of which telescopes within the front sleeve 110. The pawl sleeve 131 has a front end face 133 that engages the front sleeve stop face 118 when the pawl sleeve is fully advanced, (FIG. 3).

The pawl itself is in the form of a cantilever spring 134, the front end of which is secured to the sleeve 131 and the rear end of which is bent inwardly at 135 to provide a pawl tooth for engaging a ratchet tooth face 102. The innermost end of the pawl tooth 135 is bevelled for sliding rearwardly along the ratchet cam surfaces 104. A pawl release finger 136 projects from the rear end of the pawl. The front end portion of the pawl sleeve 131 is formed with a square slot 138 for receiving an actuating arm, to be described presently.

Pawl Actuating Mechanism

A manually operable pawl actuating mechanism progressively advances the dispensing plunger DP for sequentially forcing slugs "s" of amalgam (FIG. 4) from the tip end of the discharge head H.

Referring to FIGS. 2, 3 and 9, a bell crank dispensing lever or actuator 140 has a pivot hub 142 that mounts a pivot pin 144. The pin 144 extends through upstanding ears 146 on the front portion of the handle B. The actuator 140 has a rearwardly projecting operating arm 147 and a radially inwardly extending actuator arm 148. The inner end 149 of the actuator arm 148 projects through a slot formed in the tubular wall of handle B and into the actuating slot 138 formed in the pawl sleeve 131.

The actuator 140 is urged to its raised position by a leaf spring, the front end of which is received in a socket 152 formed in a handle B and the rear end of which is received in a socket 154 formed in the operating arm 147 of the actuator.

Fixed Pawl

In order to restrain retraction of the dispensing plunger DP during the return stroke of the plunger-advance pawl 130, a normally fixed pawl 160 is mounted in the hollow handle B. The fixed pawl comprises a cantilever spring 162, the front end of which is secured to a mounting clip 163 (FIGS. 3 and 10). The rear end of the fixed pawl is bent inwardly to provide a ratchet-restraining tooth 164. A pawl release finger 165 for the fixed pawl 160 projects laterally from the spring 162 adjacent the tooth 164.

In order to mount the fixed pawl 160 inside the handle B, the handle wall is formed with a square slot 166 (FIGS. 3 and 4) for receiving opposed spring fingers 167 that are bent inwardly from a clip plate 168. The front end of the pawl spring 162 is riveted to a mounting post 169 that projects inwardly from the clip plate 168. This construction permits mounting of the fixed pawl 160 by insertion of the spring 162 through the handle slot 166, followed by snapping the clip fingers 167 through the slot to urge the plate 168 against the outer wall of the handle.

Pawl Release Mechanism

In accordance with the present invention, it is desired to have the rear portion of the dispensing plunger DP entirely contained within the hollow handle B, without need for a rearwardly projecting plunger retraction and withdrawal knob. This construction renders it desirable to facilitate initial pushing of the plunger by grasping its front end (cap 121 removed) until the rear end or ratchet can be grasped and the plunger completely withdrawn from the handle for cleaning. To facilitate the operation just described, a pawl release mechanism is provided which releases both pawl teeth 135,164 from the plunger ratchet 100 and holds the pawls in a released position until the dispensing plunger is replaced in the handle B.

The preferred pawl release mechanism appears in FIGS. 3, 4 and 11–13. The mechanism is manually operated by a split collar 170 which partially encompasses and resiliently grips the handle (FIG. 11). Diametrically opposed lugs 172,174 (FIG. 11) are riveted to the collar 170. Collar lug 172 projects through a circumferentially extending slot 176 forming the handle wall and the inner end of the lug 172 is disposed for engagement with the moveable pawl release finger 136. Collar lug 174 projects through a companion handle slot 178 in the handle for engagement with the fixed pawl release finger 165.

When the dispenser D is set for amalgam dispensing, the pawl release collar 170 is manually rotated on the handle B to the "latch" position shown in FIGS. 11–13. The pawl release pins 172,174 are now at one end of their respective slots 176,178 and permit the pawls 130,160 to assume their ratchet engaging positions shown in FIGS. 3 and 4.

When it is desired to withdraw the two pawls from the ratchet 100 on the dispensing plunger DP, to facilitate retraction or withdrawal of the plunger, the collar 170 is grasped and rotated in a counter-clockwise direction to its "release" position, as viewed in FIG. 11. This rotates pins 172,174 against the respective pawl fingers 136, 165, withdraws the pawl teeth 135, 164 from the ratchet 100 and brings the teeth to their release position (not shown). The collar 170 is knurled to provide a manual grip and the frictional grip of the internal surface of the split collar 170 on the handle will hold the pawls in their "release" position until the collar is rotated clockwise back to its "latch" position.

Dispenser Operation

FIG. 3 shows a dispenser D with the dispensing plunger DP fully retracted and a fully loaded dispensing head H mounted on the dispenser. The bore 80 of the head contains the equivalent of six slugs a–f of amalgam A which correspond to the six slugs a–f of amalgam that were previously pushed into the bore 80 by the loader L (FIG. 1).

In the drawings, FIG. 3 is aligned with FIG. 1 so that the planes x—x of the rear end of the head H are also aligned. Indicated on FIG. 1 is a plane y—y of the front end 31 of the loading plunger LP, when the loading plunger is fully advanced to its dotted line position. Indicated on FIG. 3 is a plane y'—y' of the front end 93 of the amalgam-advancing tip 92 of the dispensing plunger DP, when the dispensing plunger is fully retracted.

By comparing FIGS. 1 and 3, it can be seen that when the planes x—x of the head H are aligned, the plane y'—y' is aligned with the plane y—y. As a result, when a fully loaded head H is transferred from the loader L to the handle B of the dispenser, the dispensing plunger tip 92 (plunger retracted) occupies the same position in the bore 80 of the head as that previously occupied by the loading plunger tip 31 when the loading plunger was advanced to the dotted line position of FIG. 1.

This relationship between the construction and operation of the loader L and of the dispenser D insures a "clean" transfer of the head H from the loader to the dispenser with no drop-out of amalgam particles during transfer. Also, after the head is mounted on the dispenser, (FIG. 3) the front face 93 of the dispenser plunger tip 92 abuts the rear end of the column of amalgam A in the bore 80 of the head. This provides precise control and "feel" and amalgam dispensing begins as soon as the actuator 140 is lowered. When a full column of amalgam is disposed in the head bore 80, cavity filling begins as soon as the actuator 140 is operated.

The first feed stroke of the dispensing plunger DP can be visualized by comparing FIG. 4 with FIG. 3. In FIG. 4, arm 147 of actuator 140 has been manually lowered, as indicated by the arrow at the end of the arm. This pivots actuator arm 148 to its forward position and advances the pawl sleeve 131 until the front face of the pawl sleeve engages the stop face 118 on the front sleeve 110. As the sleeve 131 and pawl 130, advance, pawl tooth 135 is brought against the first ratchet tooth face 102. Continued advance of the pawl 130 causes the pawl tooth 135 to advance the dispensing plunger DP through a feed stroke FS, indicated by an arrow on FIGS. 3 and 4. This forces the first slug "s" of amalgam out of the head H as shown in FIG. 4, for dispensing the slug into a tooth cavity.

If more amalgam is required, the operating arm 147 is released for spring return, retracting the pawl tooth 135 back over a cam surface 104 on the ratchet to a position behind the next rearward ratchet face 102. The frictional drag of the retracting pawl tooth 135 on a ratchet cam surface 104 can only retract the dispensing plunger DP a short distance, that is, until a ratchet face 102 engages the fixed pawl tooth 164. Further plunger retraction is prevented by the fixed pawl 160 and the parts are arranged to insure that the plunger-advancing pawl tooth 135 will always be retracted to a position behind a ratchet tooth face 102 on the ratchet 100, ready for a new dispensing stroke.

If more amalgam is required to fill a given tooth cavity or if more than one cavity is to be filled, the operating arm 147 is depressed again, ejecting a new slug of amalgam from the dispensing head H. This dispensing operation is repeated until the tooth cavity or cavities are filled for the conventional amalgam-packing operations that follow.

After the cavities have been filled, the operating arm 147 is repeatedly actuated to intermittently advance the dispensing plunger DP so that the tip 92 at the front end of the plunger forces all of the amalgam A out of the bore 80 in the head H. At this time, the forwardly facing stop face 108 formed at the rear of the dispensing plunger rod 96 will engage the rear stop face 119 of the fixed front sleeve 110. The front face 93 of the dispensing plunger tip 92 will now be flush with the discharge end of the bore 80 in the head H.

To give typical dimensions, the diameter of the bore 80 in the head is about ⅛th inch, as is the diameter of the parts that slide in that bore. Referring to the loader (FIG. 1) a longitudinal dimension "m" of the slugs a-f formed from amalgam in the loader reservoir is about ⅜ inches. The dimension "D" illustrated in FIG. 1, representing the penetration depth of the loading plunger into the bore 80, is ¾ inches. The length "x" (FIG. 3), representing the penetration of the dispensing plunger tip 92 into the bore 80, when the plunger is retracted, is also ¾ inches. The length of the charging stroke CS of the loader (FIG. 1) is 1⅛ inches. The slugs "s" discharged from the end of the head H (FIG. 4) are about 3/16 inches long. The overall length of the dispenser D, with the head assembled thereon is about 8¾ inches.

As to the materials of construction, I prefer that stressed parts which must be cleaned, such as the head H, the loading plunger LP, the dispensing plunger DP and the pawl sleeve 131 be formed by the investment casting of stainless steel. The body of the loader L and the handle B of the dispenser can be molded from a tough plastic material.

Although the best mode contemplated for carrying out the present invention has been herein shown and described, it will be apparent that modification and variation may be made without departing from what is regarded to be the subject matter of the invention as defined in the appended claims.

What we claim is:

1. A dental amalgam dispensing instrument of the type having a discharge head formed with an amalgam passage, a hollow handle for said head, a plunger having a front amalgam dispensing tip slidable in the amalgam passage of the head and a rearward extension with ratchet teeth, plunger-advancing pawl means for said ratchet teeth and actuator means for said pawl means; the improvement wherein said plunger-advancing pawl means comprises a sleeve slidably mounted in a forward portion of said handle, said sleeve surrounding said plunger, a cantilever spring projecting rearwardly from said sleeve and a pawl tooth at a rear portion of said spring.

2. The instrument of claim 1, wherein a longitudinal slot is formed in said handle, an actuator arm pivotally mounted on said handle and projecting through said slot, means for connecting the inner end of said actuator arm to said sleeve and an actuator lever for pivoting said actuator arm.

3. A dental amalgam loading assembly of the type comprising an amalgam loader unit having a body formed with a loading passage, a loading plunger slidable in said loading passage, an amalgam reservoir passage formed in said loader body and intersecting said loading passage, a replenishing plunger slidable in said reservoir passage, means for advancing said loading plunger across said passage intersection for shearing off slugs of amalgam and means for detachably mounting an amalgam receiving member on said loader unit which member has a bore for receiving the slugs of amalgam; the improvement wherein said body has a bayonet joint breech projecting forwardly from a zone adjacent said passage intersection; said amalgam receiving member comprising an amalgam dispensing head having a through bore, a discharge tip at its front end and a bayonet joint breech portion at its rear end; said loader body breech detachably receiving said breech portion of the dispensing head, said loading plunger advancing means comprising means for advancing a forward portion of the loading plunger a predetermined distance past said passage intersection, into said loader body breech and into the bore of said dispensing head at the breech portion of said head.

4. A dental amalgam dispenser of the type comprising a hollow handle having a tubular wall, connecting means at the front end of said handle for detachably mounting an amalgam discharge head, a discharge head mounted on said handle and being formed with an amalgam receiving bore, a plunger slidable in said handle, said plunger having a front amalgam-advancing tip and rearwardly disposed ratchet teeth, plunger-advancing pawl means on said handle for engaging said ratchet teeth and advancing said plunger and actuator means on said handle for advancing said pawl means; the improvement wherein said pawl means comprises a sleeve slidably mounted within a front portion of said tubular handle wall and surrounding a forward portion of said plunger, a cantilever spring pawl projecting rearwardly from said sleeve, an elongate slot formed in said handle wall and a short slot formed in said sleeve, said actuator means comprising an actuating arm projecting through the elongate slot in said handle wall and into the short slot in said sleeve.

5. A dental amalgam metering unit for pushing amalgam through a passage in an amalgam discharge head; said unit comprising a hollow handle, connecting means at the front end of said handle for mounting an amalgam discharge head, a plunger slidable in said handle, said plunger having a front amalgam-advancing tip and rearward ratchet teeth, a plunger-advancing pawl for engaging said ratchet teeth, sleeve means for slidably mounting said plunger-advancing pawl within the hollow of said handle, actuator means on said handle for advancing said sleeve means and said plunger-advancing pawl, comprising collar means rotatably mounted on said handle and lug means projecting from said collar means for engaging said pawl, rotation of said collar means causing said lug means to release said pawl.

6. A unit of claim 5; wherein said hollow handle is formed with a slot for receiving said lug means.

7. A dental amalgam metering unit for pushing amalgam through a passage in an amalgam discharge head; said unit comprising a hollow handle, connecting means at the front end of said handle for mounting an amalgam discharge head, a plunger slidable in said handle, said plunger having a front amalgam-advancing tip and rearward ratchet teeth, a plunger-advancing pawl for engaging said ratchet teeth, sleeve means for slidably mounting said plunger-advancing pawl within the hollow of said handle, actuator means on said handle for advancing said sleeve means and said plunger-advancing pawl, a plunger-restraining pawl fixed within said handle for engaging said ratchet teeth and preventing plunger retraction and means mounted on said handle for manually releasing both of said pawls from said ratchet teeth, said pawl releasing means comprising collar means rotatably mounted on said handle and two lugs on said collar means, one for releasing said plunger-advancing pawl and the other for releasing said plunger-restraining pawl.

8. A dental amalgam dispenser of the type comprising a hollow tubular handle, connecting means at the front end of said handle for detachably mounting an amalgam discharge head, a discharge head mounted on said handle and being formed with an amalgam receiving bore, a plunger slidable in said handle, said plunger having a front amalgam-advancing tip and rearwardly disposed ratchet teeth, plunger-advancing pawl means on said handle for engaging said ratchet teeth and advancing said plunger and actuator means on said handle for advancing said pawl means; the improvement wherein said plunger-advancing pawl means comprises a sleeve slidably mounted within a forward portion of said tubular handle, a cantilever spring pawl projecting rearwardly from said sleeve, means connecting said actuator means to said sleeve, a fixed pawl on said handle for restraining retraction of said ratchet teeth and pawl release means mounted on said handle for simultaneously withdrawing both of said pawls from the ratchet teeth.

9. A dental amalgam dispensing instrument of the type having a discharge head formed with an amalgam passage, a hollow handle for said head, a plunger in said handle having a front amalgam dispensing tip slidable in said amalgam passage and a rearward extension with ratchet teeth, plunger-advancing pawl means for said ratchet teeth and actuator means for said pawl means; the improvement comprising fixed pawl means for said ratchet teeth mounted in said handle for restraining plunger retraction and manually operable pawl release means on said handle for releasing both said plunger-advancing pawl means and said fixed pawl means from said ratchet teeth, said manually operable pawl release means comprising a collar rotatably mounted on said handle, opposed circumferential slots formed in said handle and lugs projecting from said collar through said slots for engaging said pawl means.

* * * * *